United States Patent [19]

Caspari

[11] 4,188,299

[45] Feb. 12, 1980

[54] OIL SOLUBLE DITHIOPHOSPHORIC ACID DERIVATIVES OF MERCAPTOTHIADIAZOLES

[75] Inventor: Gunter Caspari, Wheaton, Ill.

[73] Assignee: Standard Oil Company (Indiana), Chicago, Ill.

[21] Appl. No.: 906,849

[22] Filed: May 17, 1978

[51] Int. Cl.² .................. C10M 1/46; C10M 1/54; C07D 285/12
[52] U.S. Cl. .................. 252/46.4; 252/46.7; 252/400 A; 260/429.9; 260/431; 548/117; 548/142
[58] Field of Search .......... 260/302 E, 302 SD, 429.9, 260/431; 252/46.4, 46.7, 32.7, 400 A

[56] References Cited

U.S. PATENT DOCUMENTS

| | | | |
|---|---|---|---|
| 2,719,125 | 9/1955 | Roberts | 252/46.7 |
| 2,905,639 | 9/1959 | Krzikalla et al. | 252/46.7 X |
| 3,663,561 | 5/1972 | Blake | 260/302 SD |
| 3,687,963 | 8/1972 | Hoffman et al. | 260/302 E |
| 3,816,311 | 6/1974 | Malec | 252/46.7 |
| 3,914,241 | 10/1975 | Elliott et al. | 260/302 SD X |
| 3,920,671 | 11/1975 | Rufenacht | 260/302 E |
| 3,943,144 | 3/1976 | Meyer et al. | 260/302 E |
| 3,948,925 | 4/1976 | Perronnet et al. | 260/302 E |
| 3,980,573 | 9/1976 | Okorodudu | 252/46.7 |
| 4,069,319 | 1/1978 | Perronnet et al. | 260/302 E X |

FOREIGN PATENT DOCUMENTS

2500485 7/1975 Fed. Rep. of Germany ....... 260/302 E

*Primary Examiner*—Thomas A. Waltz
*Attorney, Agent, or Firm*—Mark J. DiPietro; Arthur G. Gilkes; William T. McClain

[57] ABSTRACT

Compounds having the structures:

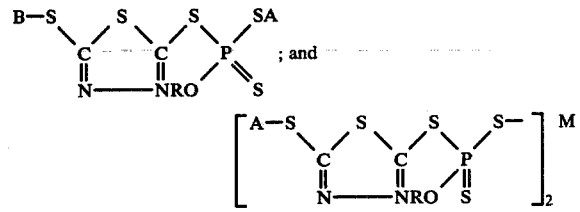

; and

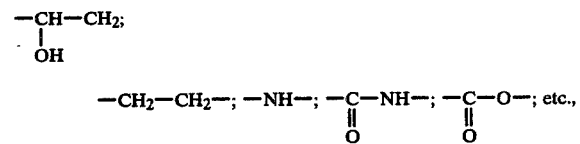

wherein B is A or a hydrogen and A is R—X; wherein X is $$-\underset{\underset{OH}{|}}{CH}-CH_2;$$

$$-CH_2-CH_2-; \quad -NH-; \quad -\underset{\underset{O}{\|}}{C}-NH-; \quad -\underset{\underset{O}{\|}}{C}-O-; \text{ etc.,}$$

M is a Group II metal cation and R is a hydrocarbyl group having about 1 to 100 carbon atoms.

18 Claims, No Drawings

OIL SOLUBLE DITHIOPHOSPHORIC ACID DERIVATIVES OF MERCAPTOTHIADIAZOLES

This invention relates to derivatives of dimercapto thiadiazole compounds. More particularly, this invention relates to the reaction product of dimercapto thiadiazole compounds, $P_2S_5$, a monohydroxy compound and a mercapto (—SH) (sulfhydryl) neutralizing compound.

There has been considerable interest in recent years in new lubricant oil additive compositions. Many of these new additive compositions are based on phosphorous compounds and sulfur compounds and mercapto thiadiazole compounds. U.S. Pat. No. 2,905,639 discloses adding to an oil about 0.01 to about 5 weight percent of an oil soluble 2,5-dimercapto-1,3,4-thiadiazole derivative corresponding to the formulae:

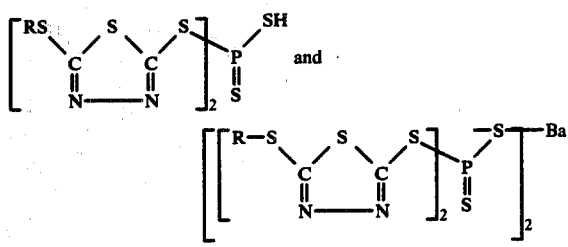

U.S. Pat. No. 3,914,241 discloses an oil soluble lubricant additive having the structure:

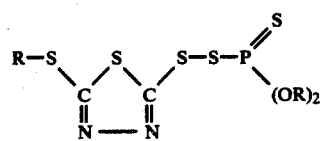

U.S. Pat. No. 3,980,573 discloses lubricant stabilized against wear and corrosion with a substituted thiadiazole having the structure:

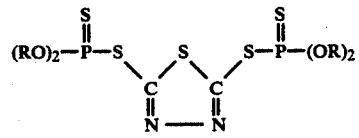

It is generally necessary to dissolve additive compositions in lubricant oils to prevent wear and corrosion. The compositions found in the patents cited above suffer from certain drawbacks. The compositions in U.S. Pat. No. 2,905,639 fail to provide substantial anti-wear properties in the lubricant. Although U.S. Pat. No. 3,914,241 discloses that certain dimercapto linked dialkyl dithiophosphate thiadiazole compounds provide anti-wear properties, and U.S. Pat. No. 3,980,573 discloses bis diallyl dithiophosphate thiadiazoles having anti-wear properties, these additives suffer from the disadvantage that they provide marginal anti-wear activity. There is need for compounds having better anti-wear activity. Further, oil additives should impart multifunctional properties to the oil. Other beneficial properties for lubricants are anti-corrosion and anti-oxidant activity.

The prior art does not disclose thiadiazole compositions which have enhanced anti-corrosion and enhanced anti-oxidant, anti-wear properties. Some prior art compounds are thiadiazole having anti-corrosion activity. Others are alkyl dithiophosphoric thiadiazoles having marginal anti-corrosion and marginal anti-wear properties, but lack the enhanced anti-wear, anti-corrosion, and anti-oxidant activity derived from various groups on the composition. Enhanced anti-wear, anti-corrosion properties of thiadiazoles permit treating the oil with smaller amounts of additive for the same level of anti-wear, anti-corrosion, and anti-oxidant activity.

Accordingly, there is a need for thiadiazoles having enhanced anti-wear, enhanced anti-corrosion and anti-oxidation properties.

Therefore, it is an object of the invention to provide a new composition of matter and processes for making the compositions. It is also an object of the invention to disclose a new additive composition having neutralized mercapto groups. It is also an object of the invention to provide new additive compositions and processes to prepare the additive composition which have multifunctional lubricant properties such as anti-corrosion, anti-oxidation, and anti-wear properties provided by the reaction product of a dimercapto thiadiazole and phosphorous pentasulfide and a monohydroxy compound having neutralized mercapto groups.

I have now found that the object of the invention can be attained by the use of the reaction product of a 2,5-dimercapto-1,3,4-thiadiazole compound, $P_2S_5$, and a monohydroxy compound, in which the thiophosphate mercapto groups are subsequently neutralized, constitute a new class of additive compositions suitable for use in lubricant oil. These compounds consist of the neutralized reaction product of 2,5-dimercapto-1,3,4-thiadiazole compound, phosphorous pentasulfide ($P_2S_5$), and a monohydroxy compound. Lubricating oil compositions containing this neutralized reaction product provide anti-wear, anti-oxidation, anti-corrosion properties, and extreme pressure properties to the lubricant oil. Compounds of this invention can be represented by the following structural formulae:

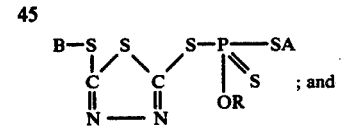

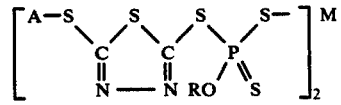

wherein B is hydrogen or A and A is a R—X, wherein X is

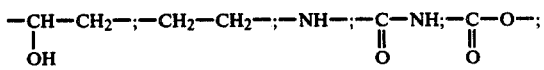

etc.; M is a group II metal cation and R is a hydrocarbyl with 1 to 100 carbon atoms.

Briefly, the compounds of this application can be prepared from a 2-substituted mercapto-5-mercapto-1,3,4-thiadiazole or unsubstituted 2,5-dimercapto thiadiazole compound of the following formulae:

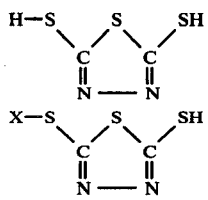

wherein X is a radical formed by the reaction of mercapto neutralizing compound and a mercapto group on the thiadiazole molecule. Compounds I or II are then reacted with phosphorous pentasulfide (P$_2$S$_5$) and a monohydroxy compound to produce an alkyl dithiophosphate thiadiazole compound with a free mercapto group. The resulting mercapto group is neutralized.

As shown above, two types of thiadiazole compounds can be reacted with P$_2$S$_5$ and a monohydroxy compound to produce compounds useful in this invention. One type is the 2,5-dimercapto-1,3,4-thiadiazole having two unsubstituted mercapto groups. The other is a 2-substituted mercapto-5-mercapto-1,3,4-thiadiazole where one mercapto group is substituted with a radical formed from a mercapto neutralizing compound. For example, 2,-hydrocarbyl-1,3,4-thiadiazole. Examples of mercapto neutralizing compounds which can be used to provide substituents at the mercapto group are olefins, carboxylic acids, carboxylic acid anhydrides, amines, forming ammonium salts, or amides. Formation of these blocking groups can be exemplified by the following illustrative sequences:

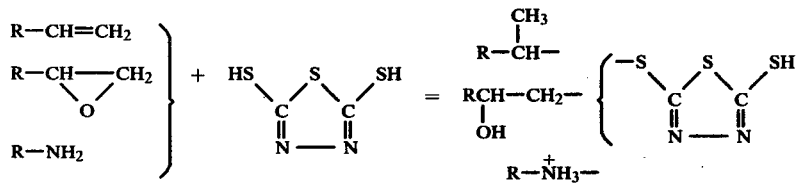

where R is an aliphatic, unsaturated, or aromatic hydrocarbon, having about 1 to 20 carbon atoms, providing oil solubility. Other reactions for neutralizing mercapto groups reactive other than these types of reactions are well known in the art and other examples of these reactions are found in *Methoden Der Organischen Chemie,* Houben-Weyl, Band XII/2, George Thieme Verlog (Stuttgart 1964), pages 692 to 812.

The monohydroxy compounds used in the reaction comprise aliphatic branched or unbranched monohydroxy compounds having from about 1 to about 40 carbon atoms, preferably from about 3 to about 20 carbon atoms. Aromatic monohydroxy compounds such as phenol substituted with a C$_{2-40}$ hydrocarbyl group are also commonly used. Monohydroxy compounds are commonly used whose hydrocarbon radicals are alkyl, cycloalkyl, arylalkyl, or aryl radicals or substantially hydrocarbon radical of similar structure. By "substantially hydrocarbon radicals" is meant radicals containing substituent groups such as ether, ester, nitro, or halogen which do not materially effect the hydrocarbon character of the radical. Specific examples of suitable monohydroxy compounds include methanol, ethanol, propanol, isopropanol, isobutanol, butanol, sec-butanol, t-butanol, hexanol, heptanol, 2-ethyl hexanol, isooctanol, nonanol, decanol, dodecanol, tetradecanol, hexadecanol, octadecanol, eicosanol, buty phenol, octyl phenol, nonyl phenol, dodecyl phenol, polyisobutene substituted phenol, tetrapropylene-substituted phenol, o-octylbutylnaphthanol, cyclopentyl phenol, cyclohexyl phenol, phenol, chlorophenol, o-dichlorophenol, bromophenol, naphthenol, 2-methylcyclohexanol, benzol, chlorobenzol, dichlorophenol, nitrophenol, etc.

Preferred monohydroxy compounds are octanol, isooctanol, isopropanol, isobutanol, nonyl alcohol, phenol, and dodecyl phenol. Phosphorous pentasulfide is a commonly available industrial chemical.

In somewhat greater detail the compositions of this invention can be prepared by the neutralization of the reaction product of phosphorous pentasulfide, the thiadiazole compound and the monohydroxy compound. The reaction can be carried out by forming a mixture in an inert solvent or oil of the three compounds added in any sequence. The reactions can be carried out at a temperature from about ambient temperature 10° C. to 200° C., preferably for ease of reaction and short reaction time at 80° C. to 150° C. At these temperatures the reactions occur readily and are complete within a period of about 30 minutes to 6 hours depending on the monohydroxy compound and the substituents on the thiadiazole compound. Certain side reactions compete with the reaction producing the dithiophosphoric acid derivatives of the mercapto thiodiazole. Principle among these reactions is the production of the dialkyl dithiophosphoric acid. Accordingly, in order to fully utilize the thiadiazole compound excesses of the monohydroxy compound and phosphorous pentasulfide, for each mole equivalent of thiadiazole compound about 0.5 to 3.0 mole equivalents of monohydroxy compound and about 0.5 to 2.0 mole equivalents of phosphorous pentasulfide are used. After the reaction unreacted compounds precipitate and are removed by decanting the reaction product from the solids.

The reaction product is then neutralized by the reaction of the mercapto neutralizing agent with the dithiophosphoric acid substituted thiadiazole compound. The mercapto neutralizing compound is added to the reaction product produced above, the neutralization compound is added dropwise or in small amounts continuously at temperature from ambient to 200° C. Generally the neutralization reaction is exothermic and in that case heating is not needed.

The addition is controlled to maintain the temperature at less than about 200° C. In some neutralization reactions water is generated. This water must be removed by blowing the reaction mixture with nitrogen at a temperature from ambient to 110° C. About 0.5 to 4.0 mole equivalents of the mercapto neutralizing compound is added per mole of the thiadiazole compound. When an unsubstituted thiadiazole compound is used, two mercapto groups are available for neutralization. Accordingly, 0.5 to 4.0 mole equivalents of mercapto neutralizing compound can be used. With a monosubstituted thiadiazole is used generally one mercapto group is available. Accordingly, 0.5 to 2.0 mole equivalents of mercapto neutralizing compound can be used.

Various solvents which can be used in this invention are hydrocarbons, hydrocarbon ethers, or chlorinated hydrocarbon solvents. Preferred solvents are benzene, toluene, pentane, hexane, heptane, octane, petroleum ether, lubricating oils, lingroin, chlorinated hydrocarbons are methyl, methylethyl, diethyl, or other mixed hydrocarbon ethers.

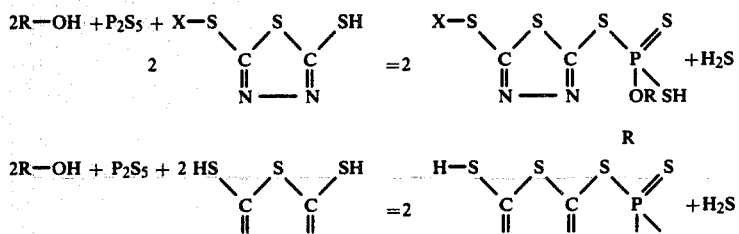

is an illustration of the reactions of an unsubstituted or a monosubstituted dimercapto thiadiazole with phosphorous pentasulfide, and monohydroxy compound.

The reaction products of an unsubstituted or a substituted mercapto thiadiazole, $P_2S_5$ and a monohydroxy compound is beneficially reacted with a compound which neutralizes the free acidic mercapto groups. Acidic mercapto groups can exist on the thiadiazole moiety or on the dithiophosphoric acid moiety. Lubricating oils are commonly alkaline substances. This alkalinity neutralizes the harmful acidic by-products of combustion and thereby protects metallic surfaces. The free acidic mercapto groups must be neutralized to prevent neutralization of beneficial alkaline components of the lubricants by the free acidic mercapto groups which would otherwise harm the properties of the lubricating oil. Any compound which will react with and neutralize the mercapto groups in the alkyl dithiophosphate or the thiadiazole may be used. Examples of such neutralizing agents are amines such as primary and secondary amines polyalkene polyamines, tertiary alkyl primary amines, and 1,6 hexane diamines. Epoxides which are available from oxidation of normal olefins or mixed olefin refinery streams may also be used to neutralize the mercapto groups. Olefins also react with mercapto groups. The reaction of a substituted 2,5-dimercapto-1,3,4-thiadiazole thiophosphoric acid derivative with an alkaline earth metal neutralization agent such as calcium oxide, a zinc oxide, or an amine may be illustrated as:

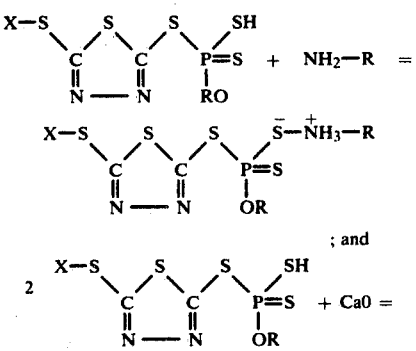

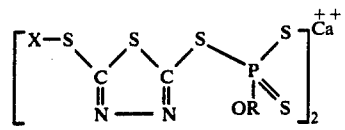

The neutralization reaction of an unsubstituted mercapto thiadiazole with neutralization agents such as amines or olefins such as styrene produce products illustrated as:

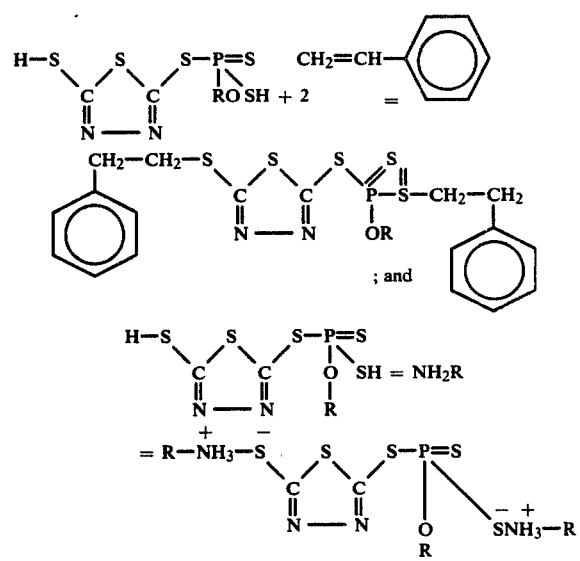

The dithiophosphoric acid derivatives of thiadiazole and the neutralized products can be prepared in batch or continuous processes. In batch processes of the solvent solution of the reactant or reactant without solvent may be added to the other reactants in a single vessel. In continuous processing, the two components in solution or solventless can be charged to different zones (countercurrent processes) or the same reaction zone, e.g., the upper end of a vertical zone maintained at a suitable elevated temperature. The product commonly is withdrawn from the other end into purification strippers and filters.

The thiadiazole derivatives of this invention are useful as lube oil additives and various oils such as synthetic, animal, vegetable or mineral oils. Ordinary lubricating mineral oils are usually preferred by reason of their availability, general excellence, and low cost. However, for certain applications other oils are preferred. For instance, synthetic polyester oils are often preferred lubricants. Normally, the lubricant oils are fluid oils the viscosity of which is greater than 4.0 Saybolt Universal seconds at 210° F., preferably greater than 40 Saybolt Universal seconds at 210° F.

This invention also contemplates the presence of other additives and lubricating compositions. Such additives include, for example, viscosity index improving agents, pour point depressing agents, antifoam agents, extreme pressure agents, rust inhibiting agents, and oxidation and corrosion inhibiting agents. The additive of this invention is generally added to lubricating oils in order to improve the corrosion inhibiting properties, oxidation inhibiting properties, and where in extreme pressure properties of said oil. Depending upon the nature of the oil and the intended use thereof and in the intended environment, different amounts of the additive are needed in order to be effective. Generally, about 0.1 to about 10 weight percent, preferably from about 0.5 to about 2 weight percent is used in the oil.

EXAMPLE I 78 grams of isooctyl alcohol (0.6 moles), 30 grams of 2,5-dimercapto-1,3,4-thiadiazole (0.2 moles) and 42 grams of $P_2S_5$ (0.2 moles) were dissolved in 20 grams of 5 weight oil which was stirred and heated to a temperature of 100° C. under an inert blanket of nitrogen in a flask equipped with a reflux condenser. After 15 minutes at 100° C., the temperature was raised to about 130° C. The mixture became clear after about 15 minutes at this temperature. The reaction was allowed to continue for an additional 30 minutes. The hot mixture was poured into a beaker where traces of unreacted solids were precipitated. The liquid product was decanted off the solids and furnished a clear, light yellow liquid. Elemental analysis showed the composition contained 11.7 percent phosphorous, 23.5 percent sulfur, and 4.9 percent nitrogen. Total acid number (TAN) was 126 (milligrams KOH/grams).

EXAMPLE II 20 gm of the product of Example 1 was placed in a flask to which was added 13 grams of a mixed, branched chain alkyl primary amine (0.04 moles) by adding the amine dropwise to the acid while the acid was being stirred.

EXAMPLE III

Example 1 was repeated with 190 grams of isodecyl alcohol (1.2 moles), 60 grams of 2,5-dimercapto-1.3,4-thiadiazole (0.4 moles) and 88 grams of $P_2S_5$ (0.4 moles) in 60 grams of 5 weight oil. The resulting clear, yellow liquid had an elemental analysis of 11.1 percent phosphorous, 23.9 percent sulfur, and 4.2 percent nitrogen. The total acid number was 89.6.

EXAMPLE IV 20 gms of product of Example 3 was neutralized in the manner of Example 2 with 12.6 grams of a mixed branched chain primary aliphatic amine (0.04 moles).

EXAMPLE V 30 grams of the composition from Example 3 was neutralized with 16 grams of oleyl amine (0.06 moles) in the manner of Example 2.

EXAMPLE VI 20 grams of the composition of Example 3 was reacted with 11.1 grams of a hydrocarbyl epoxide (0.07 moles) which is made from a mixture of C-11 to C-14 alpha-olefins.

EXAMPLE VII a. 104 grams of styrene (1.0 moles) was added dropwise to 150 grams of 2,5-dimercapto-1,3,4-thiadiazole (1.0 moles) dissolved in 50 milliliters of dioxane and a flask equipped with a dropping funnel and a reflux condenser. The mixture was heated to a temperature between 35° to 40° C. for a period of 45 minutes. The mixture is stirred under reflux for 1 hour and a solvent removed by a stream of nitrogen.

b. 156 grams of isooctyl alcohol (1.2 moles), 101.6 grams of the styrene adduct from Example VI and 88.8 grams of phosphorous pentasulfide (0.4 moles) were dissolved in 40 grams of 5 weight oil. The mixture was stirred in a flask equalled with a stirrer, heater, and reflux condenser to a temperature of 100° C. After a reaction time of 30 minutes, the temperature was raised to 132° C. and maintained for 30 minutes. The clear, yellow liquid yielded a viscous oil. The total acid number (TAN) of the product was 84 (milligrams KOH/grams).

EXAMPLE VIII 46.6 grams of the product of Example VII was added to a suspension of 8 grams of zinc oxide in 25 grams of 5 weight oil over a 10-minute period in a flask at room temperature. During the addition of the acid, the temperature rose from ambient to about 75° C. Complete neutralization was accomplished by the addition of 10 drops of nitric acid in the reaction mixture. The water of neutralization was removed by blowing the reaction mixture with nitrogen. Filtration through diatomaceous earth yielded a clear, light yellow oil whose elementary analysis was 2.9 percent zinc, 1.8 percent phosphorous, 14.9 percent sulfur, and 2.9 percent nitrogen.

EXAMPLE IX 20 grams of the composition of Example VII was reacted with 12 grams of Primene JM-T, a tertiary hydrocarbyl primary amine of a molecular weight of about 315.

EXAMPLE X 30 grams of the composition of Example VII was reacted with 11.8 grams of Needox 1114 (0.1 moles). Needox 1114 is a hydrocarbyl epoxide prepared from an oxidized mixture of C-11 to C-14 alpha-olefins.

Many variations from the examples and illustrations found above are possible. Examples and illustrations shown are to describe specific oppositions which are prepared. Those skilled in the art will be ablp to create many other variations similar to those examples found above. These examples should not be used in limiting the scope of the invention.

TABLE I

TEST FORMULATIONS

| | Compound Example at % | | | 5 Wt. Oil | Corrosion Test Solution* | Dispersant | VI-Improver | Mg Sulfonate |
|---|---|---|---|---|---|---|---|---|
| 1 | II | @ | 1% | Balance | | | | |
| 2 | IV | @ | 1% | Balance | | | | |
| 3 | VI | @ | 1% | Balance | | | | |
| 4 | IX | @ | 1% | Balance | | | | |
| 5 | VIII | @ | 1% | Balance | | | | |
| 6 | II | @ | 0.3g | | Balance | | | |
| 7 | IV | @ | 0.3g | | Balance | | | |
| 8 | V | @ | 0.3g | | Balance | | | |
| 9 | IX | @ | 0.3g | | Balance | | | |
| 10 | II | @ | 1% | Balance | | 5% | 5% | 1% |

TABLE I-continued

TEST FORMULATIONS

| Compound Example | at % | 5 Wt. Oil | Corrosion Test Solution* | Dispersant | VI-Improver | Mg Sulfonate |
|---|---|---|---|---|---|---|
| 11 IV | @ 1% | Balance | | 5% | 5% | 1% |
| 12 V | @ 1% | Balance | | 5% | 5% | 1% |
| 13 VI | @ 1% | Balance | | 5% | 5% | 1% |
| 14 IX | @ 1% | Balance | | 5% | 5% | 1% |
| 15 VIII | @ 1% | Balance | | 5% | 5% | 1% |
| 16 X | @ 1% | Balance | | 5% | 5% | 1% |
| 17 | 0% | Balance | | | | |
| 18 | 0% | | Balance | | | |
| 19 | 0% | Balance | | 5% | 5% | 1% |

*30 milliliters decalin + 1 milliliter of a 1 weight % sulfur in chloroform solution. The dispersant is a polybutyl phenol, tetraethylene pentamine, formaldehyde Mannich Base; the VI-Improver is a polyester polymer of methacrylic acid and a long chain alcohol; the Mg Sulfonate is a polypropyl benzene sulfonate overbased with MgO to a total Base No. (TBN) of about 200.

TABLE II

FOUR BALL TEST ASTM-2266**
LOAD BEARING - ANTI-WEAR TEST

| Test Formulation | Scar Diameter (mm) |
|---|---|
| 1 | 0.60 |
| 2 | 0.60 |
| 3 | 0.55 |
| 4 | 0.58 |
| 5 | 0.41 |
| 17 (no additive) | greater than 2mm after 1 min. |

**Test Condition 1,800 rmp; 0.5 hours; 30 kg load.

ASTM-2266 is a test which determines the load-bearing properties of lubricating fluids. The testing machine is operated with one steel ball rotating against three balls held stationary to form a cradle. The balls are rotated at about 1770±60 rmp at 65° to 95° F. at a certain kg-load. The test results in Table III show acceptable load bearing anti-wear properties of the anti-wear additive.

TABLE III

COPPER STRIP CORROSION TEST ASTM D-130***

| Test Formulation | ASTM Rating |
|---|---|
| 6 | 1a |
| 7 | 1a |
| 8 | 1a |
| 9 | 1b |
| 18 (no additive) | 4c |

***Modified Test Conditions 3 hours at 212° F.

The modified ASTM method D-130 is a test to detect the corrosiveness of hydrocarbons to copper. A polished copper strip is immersed in a given quantity of sample and test solution, and is heated at a temperature for a time characteristic of the material tested. At the end of the test the copper strip is washed and compared with ASTM Copper Strip Corrosion Standards. In the modified test a test solution is made of 30 milliliters of decalin and 1 milliliter of a 1 weight % sulfur in chloroform solution. 0.3 grams of the test additive is dissolved in the test fluid and the copper strip is immersed in the test fluid for the corrosion testing in other respects the test is the same.

TABLE IV

OXIDATION TEST

| Test Composition | Spot Dispersancy Test (%) After 48 Hours | (4 × VO) Time, Hours |
|---|---|---|
| 10 | 100 | 159 |
| 11 | 100 | 165 |
| 12 | 95 | 152 |
| 13 | 98 | 157 |
| 14 | 100 | 160 |
| 15 | 100 | 155 |
| 16 | 100 | 172 |
| 19 (no additive) | 43 | 47 |

Anti-oxidative properties of oil composition were measured by an oil thickening test. In this test 100 grams of test oil are oxidized at 280° F. in an open oxidation tube, while being blown with 60 cc air/minute. Oxidation is catalyzed by the addition of 5 wt% Ford VC sludge oil. Samples are taken periodically and their viscosity determined to give a viscosity-time curve. The time in hours for a four-fold increase in viscosity over the initial viscosity (4 VO) is noted; a long 4 VO indicates resistance to oil thickening by oxidation. Also, a sample of this oil after 48 hours of oxidation is run in the Spot Dispersancy Test which gives a measure of the oil's ability to disperse sludge and varnish. In the Spot Dispersancy Test, 3-10 drops of oil are dropped onto a standard white blotter paper on which is a sludge spot. After 24 hours, the diameter of the sludge spot and the oil spot are measured. Dispersancy is reflected by the ability of an oil to keep sludge in suspension. Thus, dispersancy will be reflected by the difference in diameters of the sludge and oil spots. A rating (SDT Rating) is given by the diameter of the sludge spot divided by the diameter of the oil spot, and multiplied by 100. A high numerical rating indicates good dispersancy.

I claim:

1. A compound having the structure:

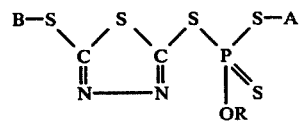

wherein B is hydrogen or A and A is R—X—; X is

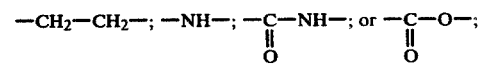

and R is a hydrocarbyl having about 1 to 100 carbon atoms.

2. A lubricating oil composition containing a major portion of a lubricating oil and about 0.1 to 10.0 weight percent of the compound of claim 1 based on the oil.

3. The compound of claim 1 wherein B is X—R wherein X is —NH—.

4. The compound of claim 1 wherein A is

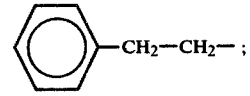

and B is —NH—R.

5. The compound of claim 1 wherein A is —NH—R and B is —NH—R.

6. A compound having the structure:

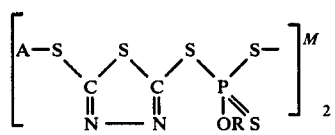

wherein M is a Group II metal and A is R—X— wherein X is $$-\underset{\underset{OH}{|}}{CH_2}-CH_2-;$$

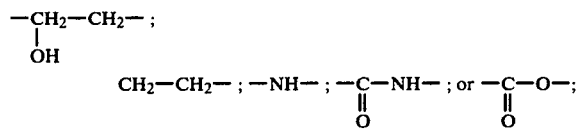

and R is a hydrocarbyl group having about 1 to 100 carbon atoms.

7. The compound of claim 6 wherein M is selected from the group consisting of calcium and zinc.

8. The compound of claim 6 wherein A is

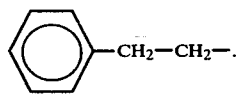

9. A lubricating oil composition containing a major portion of a lubricating oil and about 0.1 to 10.0 weight percent of the compound of claim 6 based on the oil.

10. A process for the manufacture of oil soluble compounds comprising reacting a thiadiazole compound and about 0.5 to 3.0 mole equivalents of a monohydroxy compound and about 0.5 to 2.0 mole equivalent of phosphorous pentasulfide to form a first reaction product and then reacting a 0.5 to 4.0 mole equivalents of mercapto neutralizing compound with the first reaction product per mole of the thiadiazole component in the first reaction product.

11. The process of claim 10 wherein the reaction is conducted at a temperature of about 10° C. to about 200° C. for about 1 hour.

12. The process of claim 10 wherein the reaction was conducted at a temperature of from about 80° C. to about 150° C. for about 1 hour.

13. The process of claim 10 wherein the reaction is conducted in an inert solvent.

14. The process of claim 10 wherein the thiadiazole compound is selected from a group consisting of 2,5-dimercapto-1,3,4-thiadiazole and 2-hydrocarbyl mercapto-5-mercapto-1,3,4-thiadiazole.

15. The process of claim 10 wherein said monohydroxy compound contains about 1 to about 20 carbon atoms.

16. The process of claim 9 wherein the mercapto neutralizing agent is selected from the group consisting of amines, olefins, and epoxides, each containing from about 2 to about 100 carbon atoms.

17. The process of claim 14 wherein when the thiadiazole compound is 2-hydrocarbyl mercapto-5-mercapto-1,3,4-thiadiazole, the mercapto neutralizing agent is an alkaline earth metal compound.

18. The compounds of claims 1 or 6 wherein R has 3 to 20 carbon atoms.

* * * * *